(12) United States Patent
Hofstad et al.

(10) Patent No.: US 6,219,582 B1
(45) Date of Patent: Apr. 17, 2001

(54) TEMPORARY ATRIAL CARDIOVERSION CATHETER

(75) Inventors: Michael L. Hofstad, Minnetonka; John D. Ockuly, Robbinsdale; Michael J. Coyle, Minneapolis; Mark W. Kroll, Minnetonka; Steven E. Scott, Chanhassen, all of MN (US)

(73) Assignee: Daig Corporation, Minnetonka, MN (US)

( * ) Notice: Subject to any disclaimer, the term of this patent is extended or adjusted under 35 U.S.C. 154(b) by 0 days.

(21) Appl. No.: 09/224,257

(22) Filed: Dec. 30, 1998

(51) Int. Cl.[7] ........................................ A61N 1/05
(52) U.S. Cl. ............................................. 607/122
(58) Field of Search .................... 607/119, 122, 607/123

(56) References Cited

U.S. PATENT DOCUMENTS

| | | |
|---|---|---|
| 5,044,375 * | 9/1991 | Bach, Jr. et al. ............... 607/122 |
| 5,165,403 | 11/1992 | Mehra . |
| 5,209,229 | 5/1993 | Gilli . |
| 5,231,995 | 8/1993 | Desai . |
| 5,265,623 | 11/1993 | Kroll . |
| 5,350,404 | 9/1994 | Adams et al. . |
| 5,405,375 * | 4/1995 | Ayers et al. ................... 607/122 |
| 5,423,772 | 6/1995 | Lurie et al. . |
| 5,466,254 | 11/1995 | Helland . |
| 5,545,193 | 8/1996 | Fleischman et al. . |
| 5,545,204 * | 8/1996 | Cammilli et al. ............... 607/122 |
| 5,549,661 | 8/1996 | Kordis et al. . |
| 5,571,159 | 11/1996 | Alt . |
| 5,575,810 | 11/1996 | Swanson et al. . |
| 5,582,609 | 12/1996 | Swanson et al. . |
| 5,626,136 | 5/1997 | Webster, Jr. . |
| 5,680,860 | 10/1997 | Imran . |
| 5,697,965 | 12/1997 | Griffin, III . |
| 5,720,775 | 2/1998 | Larnard . |
| 5,730,127 | 3/1998 | Avitall . |
| 5,741,322 | 4/1998 | Mehmanesh et al. . |
| 5,766,224 | 6/1998 | Alferness et al. . |
| 5,810,887 | 9/1998 | Accorti, Jr. et al. . |

OTHER PUBLICATIONS

Krum, et al., "Optimization of Shocking Lead Configuration for Transvenous Atrial Defibrillation", *Journal of Cardiovascular Electrophysiology*, vol. 9, No. 9, Sep. 1998, pp. 998–1003.

* cited by examiner

Primary Examiner—George R. Evanisko
(74) Attorney, Agent, or Firm—Scott R. Cox

(57) ABSTRACT

A coronary sinus catheter includes a distal electrode portion with optimally-spaced and sized ring electrodes and a proximal electrode portion with at least one optimally-spaced and sized larger surface electrode. The catheter has all or some of the following features. First, at least one ring electrode of the distal electrode portion includes a first diameter less than a second diameter of at least one, more proximally disposed, ring electrode of the distal electrode portion. Second, at least one ring electrode of the distal electrode portion includes a first width less than a second width of at least one, more proximally disposed, ring electrode of the distal electrode portion. Third, the distal electrode portion includes at least two ring electrodes and the proximal shock electrode includes at least two larger surface coil electrodes. Fourth, the catheter further includes a collapsible section, adjacent the proximal electrode portion, to facilitate positioning of the catheter within the right atrium.

34 Claims, 4 Drawing Sheets

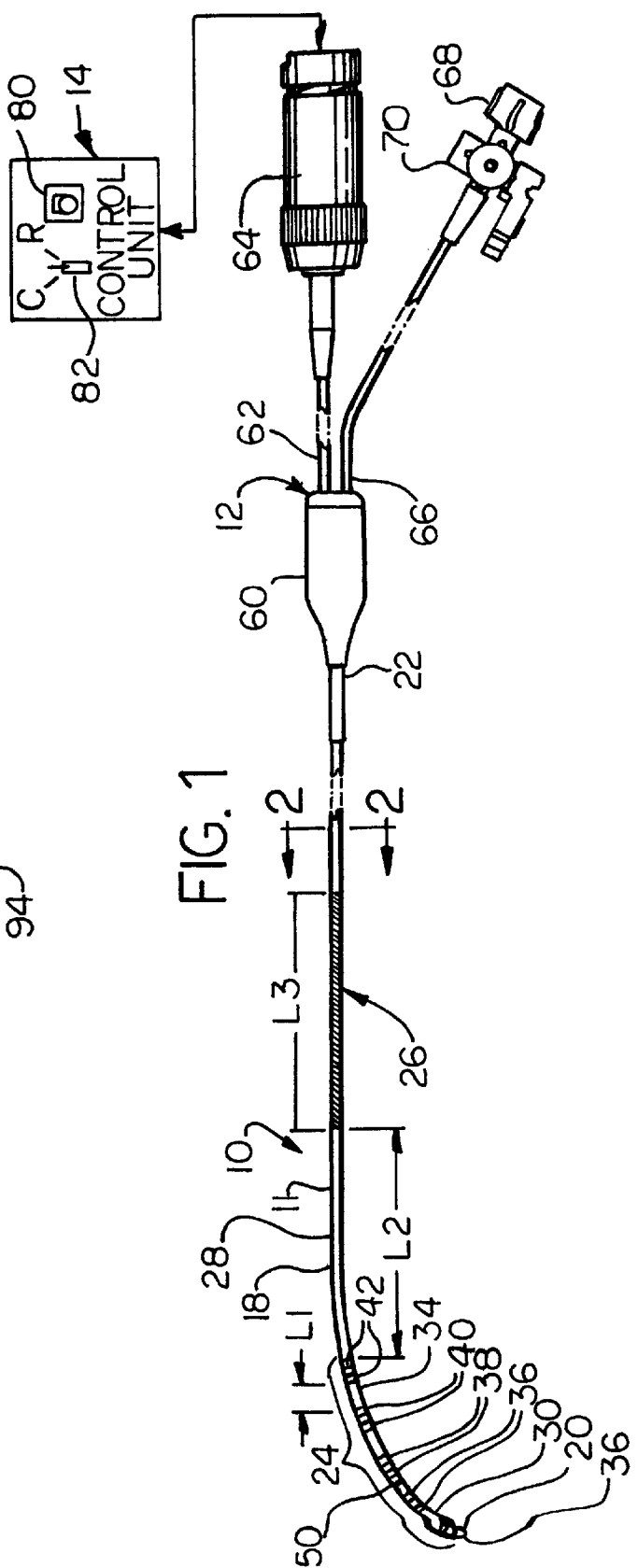
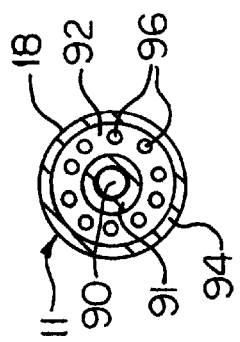
FIG. 1
FIG. 2

TEMPORARY ATRIAL CARDIOVERSION CATHETER

BACKGROUND OF THE INVENTION

The present invention relates to cardiovascular catheters. In particular, the present invention relates to a catheter for temporary placement in the coronary sinus and right atrium for atrial cardioversion.

Electrophysiology (EP) catheters are well recognized and important tools for performing a variety of functions such as recording the heart's electrical signals, pacing the heart, or cardioverting the heart. For recording electrical activity in the heart, EP catheters are used to record intracardiac electrograms. When positioned in the heart, an EP catheter records the electrical activity between a pair of electrodes at the distal end of the catheter to provide a recordation of the electrical activity of a localized area of the heart near the electrode pair. By using multiple EP catheters positioned in the heart, one can map the sequence of myocardial depolarization as an electrical impulse traverses the heart.

EP catheters may also be used for pacing and/or cardioversion. For pacing, a pulse of electrical current is carried by the catheter from an external pacemaker to the heart where it causes cardiac cells near the catheter's electrodes to depolarize. The depolarization of these cardiac cells is then propagated across the heart as if the impulse arose from the heart itself. For cardioversion, a high energy electrical charge is applied to the heart using an EP catheter causing instant and rapid depolarization of all cardiac cells in an attempt to restore the heart to normal sinus rhythm.

Current EP catheters include distal portions having a variety of ring electrodes, tip electrodes, coil electrodes, and large surface electrodes. Moreover, some systems include multiple EP catheters. Despite the variety of catheter components and combinations of these components on one or more EP catheters, no prior art catheter(s) has yet achieved an optimal arrangement of electrically-active components for a coronary sinus catheter for atrial cardioversion.

SUMMARY OF THE INVENTION

The present invention provides a coronary sinus catheter including a distal electrode portion with optimally-spaced and sized ring electrodes and a proximal electrode portion with at least one optimally-spaced and sized larger surface electrode. This catheter reduces energy thresholds for efficacious atrial defibrillation and allows for strategically-placed, multiple defibrillation vectors with a single catheter. The catheter further includes at least two distal curve portions to facilitate placement of the distal electrode portion within the coronary sinus and the proximal electrode portion within the right atrium and/or other vessels.

The catheter has all or some of the following features. First, at least one ring electrode of the distal electrode portion includes a first diameter less than a second diameter of at least one, more proximally disposed, ring electrode of the distal electrode portion. Second, at least one ring electrode of the distal electrode portion includes a first width less than a second width of at least one, more proximally disposed, ring electrode of the distal electrode portion. Third, the distal electrode portion includes a first, hook-type distal curve and a second, smoother proximal curve. Fourth, the distal electrode portion includes at least two ring electrodes and the proximal electrode portion includes at least two larger surface coil electrodes. Fifth, the catheter further includes a collapsible section, adjacent the proximal electrode portion, to facilitate positioning of the catheter within the right atrium.

With these features, a coronary sinus catheter of the present invention is uniquely adapted to deliver electrical signals for monitoring and defibrillation of the right atrium and coronary sinus region.

BRIEF DESCRIPTION OF THE DRAWINGS

FIG. 1 is a schematic plan view of a catheter of the present invention.

FIG. 2 is a sectional view of the catheter of FIG. 1 taken along lines 2—2.

DETAILED DESCRIPTION OF THE PREFERRED EMBODIMENTS

Figure 3:
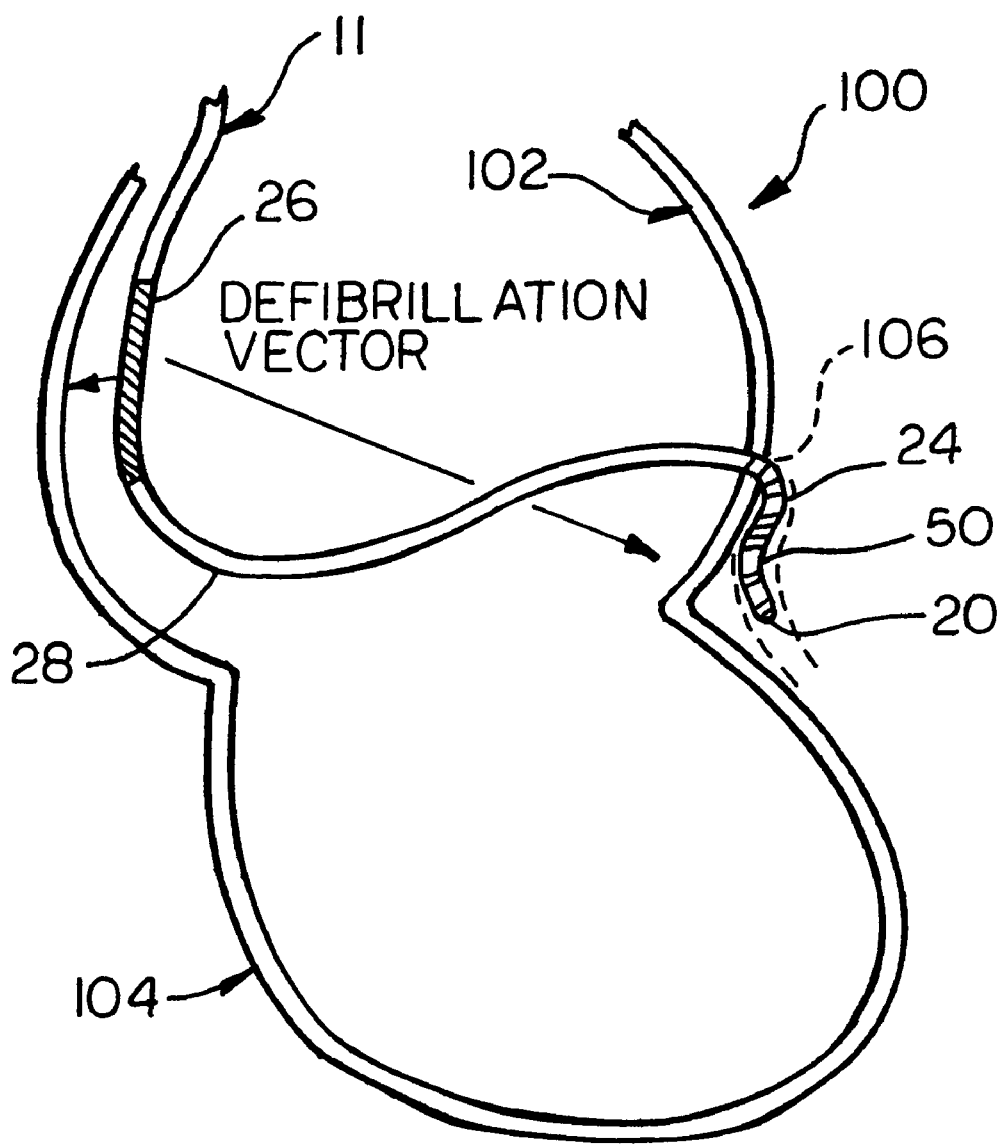
FIG. 3 is a schematic drawing of the catheter of FIG. 1 as deployed in the coronary sinus and right atrium.

A temporary atrial cardioversion system 10 is shown generally in FIG. 1. System 10 includes catheter 11, adapter 12, and control unit 14. Catheter 11 includes elongate flexible body 18 extending between distal end 20 and proximal end 22. Catheter 11 also includes distal electrode portion 24 and proximal electrode portion 26, separated by non-conductive region 28, as well as first curve 30 and second curve 34.

Distal electrode portion 24 includes first pair of distal ring electrodes 35, second pair of distal ring electrodes 36, as well as third, fourth, and fifth pairs of proximal ring electrodes 38, 40, and 42, respectively. Transition region 50 is located between distal ring pair 36 and proximal ring pair 38.

Adapter 12 further includes manifold 60, cable 62, and connector 64, as well as fluid lumen 66, connector 68, and stop cock 70. Control unit 14 includes connector 80, switch 82, and defibrillation circuitry (not shown) as is known in the art.

Examining distal electrode portion 24 in greater detail, the rings of each ring electrode pairs 35, 36, 38, 40, and 42 are spaced apart from each other about 2 millimeters. Each individual ring of ring electrode pairs 35 and 36 has a width of about 1 millimeter, while each ring of ring electrode pairs 38, 40, and 42 has a width of about 2 millimeters. Ring electrode pairs 35, 36, 38, 40, and 42 are spaced apart a distance (L1) of about 8 millimeters from each other pair along catheter body 18. Transition region 50 is located proximally about 1 inch from distal tip 20.

A portion of distal electrode portion 24 that is distal to transition region 50, and which includes distal ring electrode pairs 35 and 36, has a diameter of about 6 French. The portion of distal electrode portion 24 that is proximal to transition region 50, and which includes proximal ring electrode pairs 38, 40, and 42, has a diameter of about 7 French. The smaller diameter portion facilitates advance of catheter 11 into the coronary sinus 106 (and cardiac vein), as seen in FIG. 3, while the larger diameter portion increases the strength of catheter 11 in more proximal regions. The larger diameter of proximal ring electrode pairs 38, 40, 42 decreases defibrillation thresholds while their larger width of 2 millimeters (compared to a 1-millimeter width of distal ring pairs 35, 36) increases the current passing through them. Transition region 50 forms a transition between the smaller diameter distal portion and the larger diameter proximal portion of distal electrode portion 24.

Non-conductive region 28, which separates distal electrode portion 24 from proximal electrode portion 26, has a length (L2) of approximately 6 to 10 centimeters extending from the most proximal ring of ring electrode pair 42 to a distal end of proximal electrode portion 26. However, the length of non-conductive region 28 can vary between 6 and 10 centimeters to accommodate varying patient anatomies.

Proximal electrode portion 26, preferably has a length (L3) of about 6 centimeters and is preferably formed of a wound platinum coil wire to provide a low-impedance path for a cardioversion shock. However, other large surface non-coil electrodes can be used. Proximal electrode portion 26 preferably has a diameter of about 7.5 French to further reduce impedance.

Manifold 60 is connected to, and is in communication with, proximal end 22 of catheter body 18. In particular, manifold 60 includes a multi-lumen structure for permitting passage of conductive components of cable 62 and fluid within lumen 66 to pass through manifold 60 for communication with corresponding lumens within catheter body 18. As will be described in greater detail below with reference to FIG. 2, at least one fluid lumen and multiple conductors from conductive cable 62 extend through catheter body 18 for communication with appropriate ring electrode pairs 35, 36, 38, 40, and 42 and fluid ports. Conductive cable 62 extends proximally from manifold 60 for communication with connector 64, which is removably securable to a reciprocating, multiple conductor pin connector 80 of control unit 14. Fluid lumen 66 also extends proximally from manifold 60 for fluid communication with stop cock 70 and connector 68, which is adapted for removable connection to a fluid-injection source (not shown). For example, fluid lumen 66 can be used for delivering radiopaque fluid to permit guidance of catheter 11 under fluoroscopy or for delivery of drugs within the vascular system. Stop cock 70 selectively regulates passage of fluid through fluid lumen 66.

Control unit 14 includes known circuitry for electrophysiology, pacing, and cardioversion/defibrillation. Control unit 14 further includes switch 82 for selecting at least a cardioversion mode and a monitoring/diagnostic mode for operating catheter 11 within a cardiovascular system. Control unit 14 permits operating ring electrode pairs 35, 36, 38, 40, and 42 independently for cardiac mapping or pacing, or together in series to act as a single electrode for defibrillation/cardioversion.

Catheter body 18 is shown in cross section in FIG. 2. In particular, catheter body 18 includes fluid lumen 90 defined by inner wall 91 and conductor lumen 92 defined by both inner wall 92 and outer wall 94. A plurality of conductors 96 extend through a length of lumen 92 within catheter body 18 from catheter proximal end 22 to catheter distal end 20 for connection to a corresponding ring of ring electrode pairs 35, 36, 38, 40, 42 or proximal electrode coil 26. The arrangement shown in FIG. 2 is merely an example as many configurations of a fluid lumen and multiple conductor/conductor lumens can be used to pass fluid and electrical current from proximal end 22 of catheter 11 to distal end 20.

In operation, as shown in FIG. 3, catheter 11 is deployed within a cardiovascular system for placement within right atrium 102 of heart 100. Heart 100 further includes right ventricle 104, and coronary sinus/cardiac vein 106. Catheter 11 is advanced through the vascular system of the patient using a guide catheter (not shown) as known in the art until catheter distal end 20 enters right atrium 102. Catheter 11 is then further maneuvered using fluoroscopy (by delivering radiopaque fluid via fluid lumen 90) so that catheter distal end 20 enters coronary sinus 106 to permit advancement of distal electrode portion 24 within coronary sinus/cardiac vein 106. Catheter 11 is advanced into this position as known in the art and as described in commonly-assigned Lurie, et al., U.S. Pat. No. 5,423,772, titled: CORONARY SINUS CATHETER, which is expressly incorporated by reference herein in its entirety.

Catheter 11 is positioned with distal electrode portion 24 within coronary sinus 106 and non-conductive region 28 extending across the right atrium so that proximal electrode coil portion 26 is adjacent to and/or is forced against a wall of right atrium 102 as shown. Control unit 14 (see FIG. 1) is manipulated to activate ring electrode pairs 35, 36, 38, 40, and 42 of distal electrode portion 24 within coronary sinus/cardiac vein 106 to obtain diagnostic information about cardiac electric pathways of the heart. In this mode, each ring of the ring electrode pairs 35, 36, 38, 40, and 42 operates independently. However, when it is desired to defibrillate right atrium 102, switch 82 on control unit 14 is used to select the defibrillation mode for control unit 14 thereby causing ring electrode pairs 35, 36, 38, 40, and 42 to be electrically-connected in series to act as one large electrode. Using control unit 14, a defibrillation electrical signal is applied through distal electrode portion 24, acting as a cathode, and proximal electrode portion 26, acting as an anode. As shown in FIG. 3, this arrangement produces a defibrillation vector through the atrial septum and a portion of the exterior atrial walls. Control unit 14 also can be operated so that distal electrode portion 24 acts as the anode, and proximal electrode portion 26 acts as the cathode to direct the defibrillation vector in an opposite direction.

Catheter 11 of the present invention provides numerous advantageous features. Distal electrode portion 24 includes ring electrode pairs 35, 36, having a narrower first width and a smaller first diameter than ring electrode pairs 38, 40, 42. This arrangement in the more distal portions of catheter 11 enhances entry and positioning of catheter 11 into the coronary sinus/cardiac vein 106 and application of current in the coronary sinus/cardiac vein 106. In particular, the smaller diameter portion of distal electrode portion 24 is thinner and more flexible, allowing further penetration into the distal coronary sinus and cardiac vein while its narrower ring electrodes (1-millimeter width) reduce the current that passes through the more fragile distal coronary sinus and cardiac vein. In contrast, the larger diameter portion of distal electrode portion 24 is thicker and less flexible, increasing strength in catheter 11, while its larger diameter ring electrodes decreases defibrillation thresholds and its greater width ring electrodes increase the current passing through them into the cardiac tissue.

Figure 4:
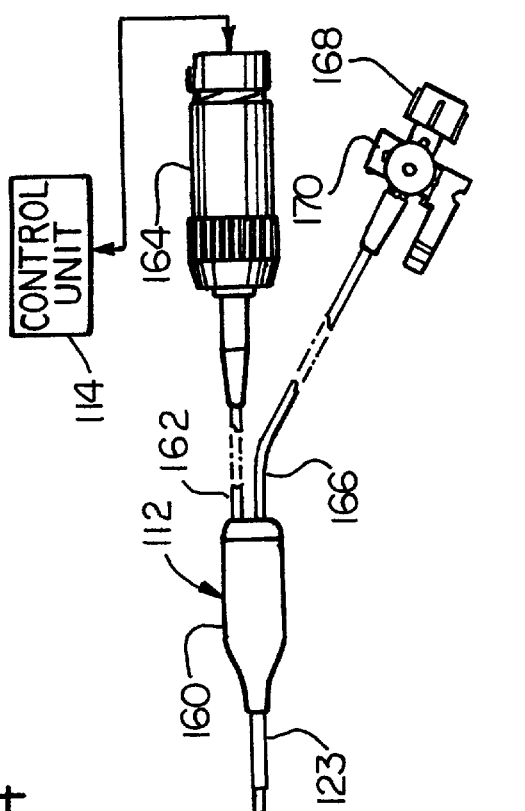
FIG. 4 is a schematic plan view of another embodiment of a catheter of the present invention.

An alternate embodiment of a temporary atrial cardioversion catheter of the present invention is shown generally in FIG. 4. System 110 includes catheter 111, adapter 112, and control unit 114. Catheter 111 includes flexible catheter body 118, distal end 122 and proximal end 123, with distal electrode portion 124 and proximal electrode portion 126 separated by non-conductive portion 155. Catheter body 118 includes first curve 130, second curve 132, collapsible region 134, and transition region 150. Distal electrode portion 124 includes distal ring electrode pairs 135 and 136, as well as proximal ring electrode pairs 138, 140, and 142.

Proximal electrode section 126 includes first coil electrode 152 and second coil electrode 154, separated by non-conductive region 155. Non-conductive region 155 has a length of approximately 6 to 10 centimeters, while coil electrodes 152 and 154 each have a length of about 6 centimeters. System 110 further includes manifold 160, conductive cable 162, connector 164, as well as fluid lumen 166, connector 168 and stop cock 170.

Except for the addition of collapsible region 134 and a second, more proximal coil electrode 154, catheter 111 and system 110 have substantially the same features and attributes as catheter 11 and system 10, as described in connection with FIGS. 1–3. However, these added features of collapsible region 134 and coil electrode 154 greatly affect the manner of operation of catheter 111, as compared to catheter 11.

Figure 5:
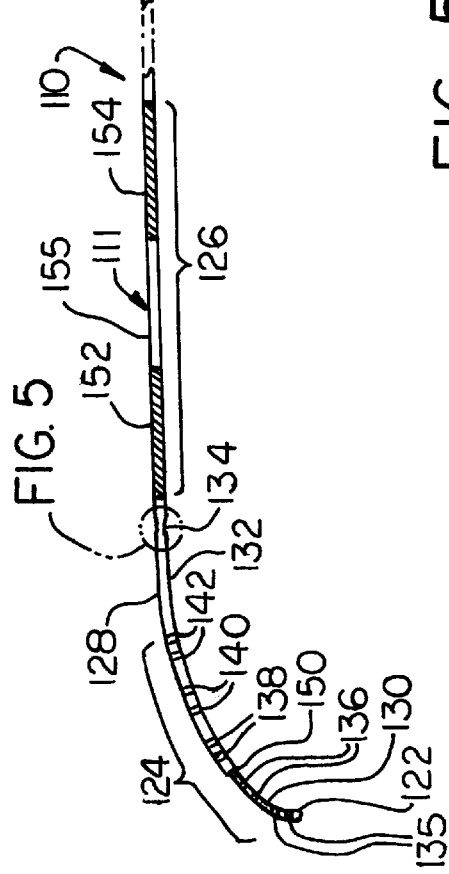
FIG. 5 is an enlarged sectional view of a portion of the catheter of FIG. 4.

Catheter 111 includes a lumen structure substantially similar to that shown in FIG. 2 for catheter 11. However, as shown in FIG. 5, collapsible region 134 includes outer catheter wall 180 (for illustrative purposes, an inner catheter wall like wall 91 in FIG. 2 is not shown) that is corrugated or thinner, and/or that omits reinforcing material in the catheter wall sufficient to permit the catheter to be bent more easily at that location. In one example, catheter body 118 has a mutli-layer wall that includes a braided reinforcing material that extends the length of catheter body 118 except at collapsible region 134, where the braid is interrupted or omitted over the length of collapsible region 134. Alternatively, collapsible region 134 is defined by a bond member that is free of reinforcing material and that is secured between two separate braided shafts of the catheter which extend distally and proximally, respectively, from the bond member to define catheter body 118.

Figure 6:
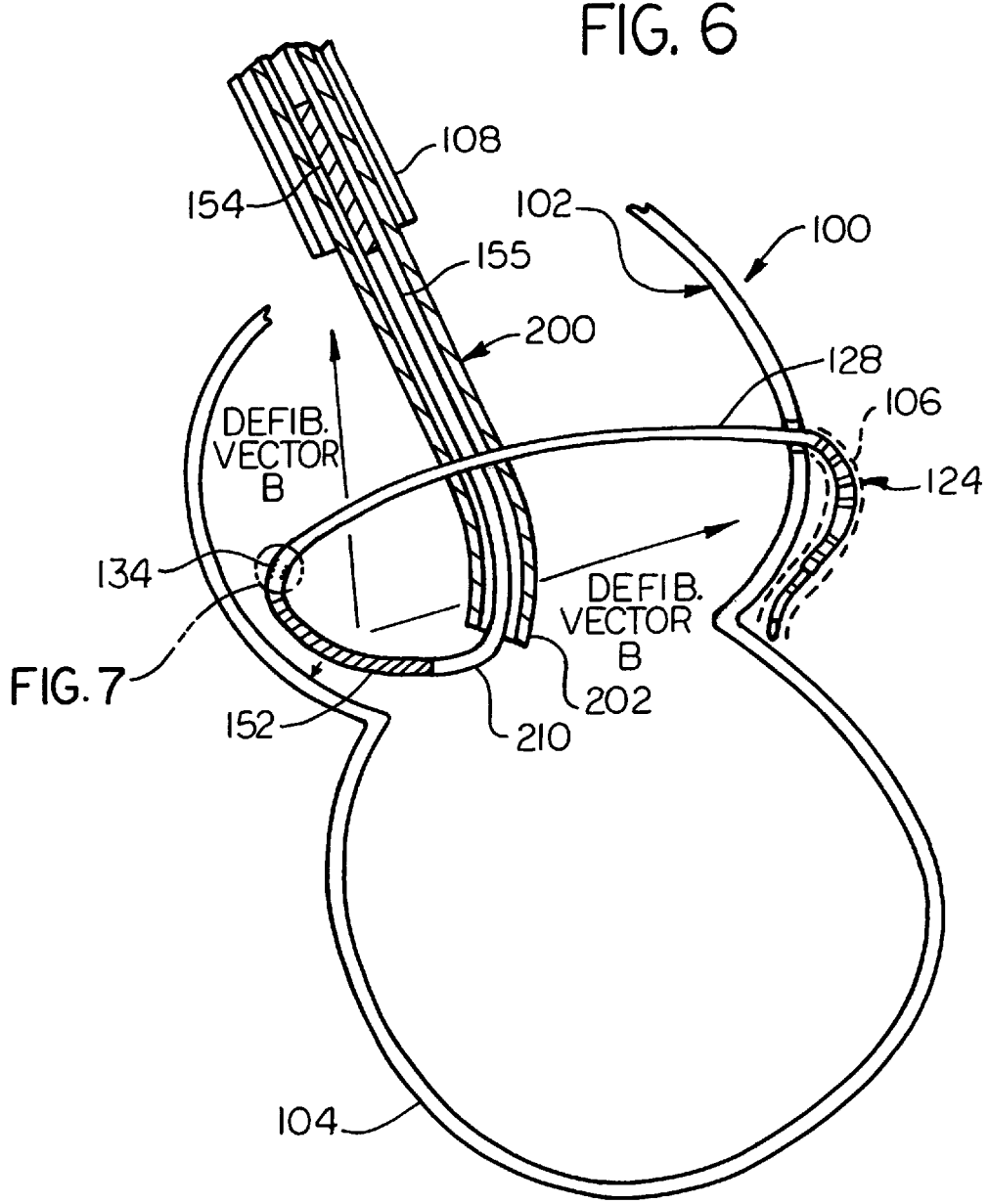
FIG. 6 is a schematic drawing of a catheter of an alternate embodiment of the present invention deployed in the coronary sinus, right atrium, and superior vena cava.

In operation, as shown in FIG. 6, catheter 111 is inserted into the right atrium and coronary sinus 106 in a manner similar to that described in connection with FIG. 3. In particular, catheter 111 is maneuvered so that distal electrode portion 124 extends within coronary sinus 106 (and cardiac vein) with non-conductive portion 128 extending across right atrium 102. However, as shown in FIG. 6, guide catheter 200 plays a prominent role in positioning catheter 111 within right atrium 102. Using distal end 202 of guide catheter 202, coil electrode 152 is forced toward the right atrial appendage of right atrium 102 with collapsible region 134 facilitating the bending of catheter 11 into this position. By further distally advancing distal end 202 of guide catheter 200, a temporary bend in catheter body 118 is also forced at location 210, just proximal to coil 154 to cause the remaining proximal portion, including non-conductive region 152, to extend upwardly through right atrium so that proximal coil electrode 154 extends within the superior vena cava.

With catheter 111 placed in this arrangement within right atrium 102, as shown in FIG. 6, control unit 114 is activated so that ring electrode pairs 135, 136, 138, 140, and 142 of distal electrode portion 124 are electrically connected in series as one large electrode. Next, a defibrillation electrical signal is applied to catheter 111, producing two defibrillation vectors A and B, originating from coil electrode 152 (acting as an anode), directed simultaneously both to coil electrode 154 and to ring electrode pairs 135, 136, 138, 140, and 142 of distal electrode portion 124 (both acting as cathodes).

Deploying catheter 111 in this manner permits a simultaneous application of two defibrillation vectors A and B to more effectively defibrillate the right atrium to terminate atrial defibrillation. This three-electrode arrangement reduces energy thresholds for achieving efficacious atrial defibrillation as compared to a two electrode arrangement. Moreover, while FIG. 6 illustrates first coil electrode 152 acting as an anode and distal electrode portion 24 with second coil electrode 154 acting as a cathode, control unit 114 can be operated to selectively designate the polarity of first and second electrode coil segments 152, 154 and distal electrode portion 24 to produce other cathode/anode combinations.

Figure 7:
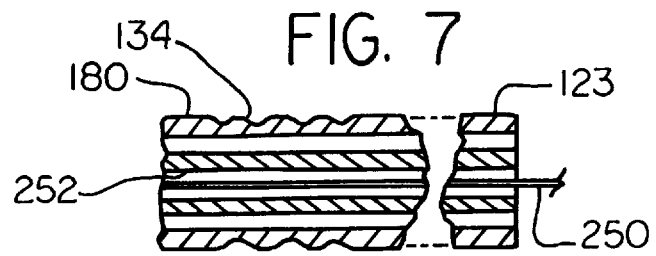
FIG. 7 is an sectional view of a portion of the catheter of FIG. 4 with an optionally deployed guide wire.

During advancement of catheter 111 into and through guide catheter 200 and right atrium 102, a relatively stiff guide wire or stylet 250 is optionally removably disposed within an inner lumen 252 (like lumen 91 of catheter 11 as shown in FIG. 2) of catheter 111 as shown in FIG. 7 for maintaining sufficient rigidity in collapsible region 134 during positioning of catheter 111. In particular, guide wire 250 selectively extends both proximally and distally of collapsible region 134 to maintain the desired rigidity during placement of catheter 111 within coronary sinus 106 and adjacent the right atrial appendage of right atrium 102. Just prior to selective bending of collapsible region 134 (see FIG. 6), a distal end of guide wire 250 is positioned proximally relative to collapsible region 134 to permit the selective bending step to occur. Guide wire 250 has a length sufficient to extend proximally from distal regions of catheter 111, such as collapsible region 134, to manifold 160. Accordingly, guide wire 250 extends proximally outward from manifold 160 through a lumen within manifold 160 (not shown) that is in communication with inner lumen 252 and fluid lumen 166 so that guide wire 250 can extend proximally outward from lumen 166 for manipulation. Of course, a proximal end of lumen 166 can be adapted as necessary, as known to those skilled in the art, to permit insertion, removal, and manipulation of guide wire 250 through lumen 166. Finally, catheter 111 optionally can includes other inner lumen configurations to permit the use of guide wire 250 and/or injection of a fluid (e.g., radiopaque fluid or medicants).

A catheter of the present invention provides numerous advantageous features. This catheter of the present invention includes a distal electrode portion having a smaller first diameter portion and a larger, second diameter more proximal portion. This arrangement, in the more distal portions of the catheter, allows further penetration of the catheter into the coronary sinus/cardiac vein 106. Narrower ring electrodes in the most distal portions of the catheter reduce the current that passes through the more fragile distal coronary sinus and cardiac vein. In contrast, wider ring electrodes in the larger diameter proximal portion increases the current passing into the cardiac tissue.

Moreover, a three-electrode catheter of the present invention, in which the group of ring electrodes and the two proximal coil electrodes are activated in various cathode/anode combinations, reduces the energy thresholds for achieving atrial defibrillation. Finally, the catheter of the present invention optionally includes a collapsible section adjacent one of the electrodes to ease placement of the adjacent electrode against a wall of the right atrium.

Although the present invention has been described with reference to preferred embodiments, workers skilled in the art will recognize that changes may be made in form and detail without departing from the spirit and scope of the invention.

What is claimed:

1. An atrial cardiovascular catheter comprising:
an elongate flexible member comprising:

an electrically active distal portion defining a first diameter;

an electrically active intermediate portion spaced proximally from the distal portion and defining a second diameter greater than the first diameter;

a first coil electrode proximally spaced about 6 to about 10 centimeters from the intermediate portion, and a second coil electrode which is proximally spaced about 6 to about 10 centimeters proximally from the first coil electrode.

2. The catheter of claim 1 wherein the elongate flexible member further comprises:

a collapsible section for permitting an acute angle to be formed between adjacent sections of the catheter on opposite sides of the collapsible section.

3. The catheter of claim 2 wherein the collapsible section is disposed distal to the first coil electrode proximal portion.

4. The catheter of claim 1 wherein the first diameter is about 6 French size and the second diameter is about 7 French size.

5. An atrial cardiovascular catheter comprising an elongate flexible member comprising:

an electrically active distal portion defining a first diameter; and an electrically active intermediate portion spaced proximally from the distal portion defining a second diameter which is greater than the first diameter;

wherein the distal portion further comprises at least one ring electrode, wherein the intermediate portion further comprises at least one ring electrode, and wherein the at least one ring electrode in the distal portion has a first width that is less than a second width of the at least one ring electrode in the intermediate portion.

6. The catheter of claim 5 wherein the first width is about 1 millimeter and the second width is about 2 millimeters.

7. The catheter of claim 5 further comprising a first coil electrode, wherein the first coil electrode has a third width different than the first width and the second width.

8. The catheter of claim 5 wherein the distal portion comprises four ring electrodes.

9. The catheter of claim 8 wherein the four ring electrodes are defined as a first set of two ring electrodes and a second set of two ring electrodes wherein the ring electrodes of the first set, and the ring electrodes of the second set, are spaced apart from each other about 2 millimeters, and the first set is located more distally than the second set and the proximal ring electrode of the first set is located about 8 millimeters from the distal ring electrode of the second set.

10. The catheter of claim 9 wherein that portion of the distal portion containing the first set of ring electrodes define an angle of about 30 to 50 degrees relative to that portion of the distal portion containing the second set of ring electrodes.

11. The catheter of claim 5 wherein the intermediate portion comprises six ring electrodes defined as a first set of two ring electrodes, a second set of two ring electrodes, and a third set of two ring electrodes wherein the ring electrodes of each set are spaced apart about 2 millimeters, and the first set is located more distally than the second set and a proximal ring electrode of the first set is located about 8 millimeters from a distal ring electrode of the second set, and a proximal ring electrode of the second set of ring electrodes is located about 8 millimeters from a distal ring electrode of the third set of ring electrodes.

12. The catheter of claim 5 wherein the distal portion and the intermediate portion each comprise at least one ring electrode and wherein each of the ring electrodes is connected to a conductor secured to the elongate flexible member that extends from the ring electrode to a proximal end of the catheter for electrical connection to a control unit external of a body of a patient.

13. A medical device comprising the catheter of claim 5 and further comprising a control unit selectively operable in a first mode in which conductors within the catheter are selectively connected together to electrically connect ring electrodes contained in the distal portion and the intermediate portion in series in a first mode and in a second mode in which the conductors are controlled independently to operate each ring electrode independently.

14. The catheter of claim 5 wherein the elongate flexible member further comprises a fluid lumen throughout the length of the elongate flexible member, wherein the lumen has at least one distal port in communication with the lumen.

15. An atrial cardioversion catheter comprising an elongated flexible member comprising an electrically active distal portion defining a first diameter; and an electrically active intermediate portion spaced proximally from the distal portion and defining a second diameter greater than the first diameter, wherein a first curve of the elongate flexible member forms a junction between the distal portion and the intermediate portion and has a radius of curvature of about 7 to about 11 centimeters with an arc of about 30 to about 50 degrees and a second curve of the elongate flexible member defines the intermediate portion and has a radius of curvature of about 0.5 centimeters to about 2 centimeters with an arc of about 45 to about 90 degrees.

16. The catheter of claim 15 further comprising a first coil electrode proximally spaced from the intermediate portion.

17. The catheter of claim 15 further comprising a first coil electrode proximally spaced from the intermediate portion and a second coil electrode proximally spaced from the first coil electrode.

18. The catheter of claim 15 further comprising a collapsible section for permitting an acute angle to be formed between adjacent sections of the catheter on opposite sides of the collapsible section.

19. The catheter of claim 18 wherein the collapsible section is disposed distally from the first coil electrode section.

20. The catheter of claim 15 wherein the distal portion further comprises at least one ring electrode and the intermediate portion further comprises at least one ring electrode.

21. The catheter of claim 20 wherein the at least one ring electrode in the distal portion has a first width that is greater than a second width of the at least one ring electrode in the intermediate portion.

22. The catheter of claim 20 wherein the at least one ring electrode in the distal portion has a first width that is less than a second width of the at least one ring electrode in the intermediate portion and wherein the catheter further comprises a first coil electrode that has a third width different from the first width and the second width.

23. An atrial catheter for electrophysiology, pacing, or cardioversion comprising:

an elongate flexible member including:

a distal portion including at least one ring electrode;

an intermediate portion spaced proximally from the distal portion and including at least one ring electrode;

a first proximal coil electrode segment being spaced proximally from the intermediate portion; and a second proximal coil electrode segment being spaced proximally from the first proximal coil electrode segment.

24. The atrial catheter of claim 23 wherein the first coil electrode is proximally spaced about 6 to about 10 centimeters proximally from the intermediate portion.

25. The atrial catheter of claim 23 wherein the second proximal coil electrode is spaced about 6 to about 10 centimeters proximally from a proximal end of the first coil electrode.

26. The atrial catheter of claim 23 wherein an elongate flexible member further comprises a collapsible section permitting an acute angle to be formed between adjacent sections of the catheter on opposite sides of the collapsible section.

27. The atrial catheter of claim 26 wherein the collapsible section is disposed distally to the first coil electrode segment.

28. The atrial catheter of claim 23 wherein the distal portion has a first width that is less than a second width of the intermediate portion.

29. The atrial catheter of claim 28 wherein the first proximal coil electrode segment has a third width different from the first and second width.

30. The atrial catheter of claim 23 wherein the distal portion of the elongate flexible member defines an angle of about 30 to about 50 degrees relative to the intermediate portion of the elongate flexible member.

31. The atrial catheter of claim 23 further comprising a fluid lumen.

32. The atrial catheter of claim 23 wherein the elongate flexible member further comprises a first curve with an arc of about 30 to about 50 degrees and a second curve with an arc of about 45 to about 90 degrees.

33. An atrial catheter for electrophysiology, pacing, or cardioversion comprising:
   an elongate flexible member including:
      a ring electrode segment with a distal portion defining a first diameter and including at least two ring electrodes, each having a width of about 1 millimeter and a proximal portion defining a second diameter greater than the first diameter and including at least two ring electrodes, each having a width of about 2 millimeters; and
      a first coil electrode segment having a width of about 6 centimeters and being spaced proximally about 6 to about 10 centimeters from the most proximal ring electrode of the proximal portion; and
      a second coil electrode segment having a width of about 6 centimeters and being spaced proximally about 6 to about 10 centimeters from the proximal end of the first coil segment.

34. An atrial catheter for electrophysiology, pacing, or cardioversion comprising:
   a ring electrode segment having:
      a distal portion defining a first diameter and including at least two ring electrodes with each ring electrode having a first width; and
      a proximal portion defining a second diameter greater than the first diameter and including at least two ring electrodes, each ring electrode having a second width different than the first width; and
      a coil electrode segment having a width substantially greater than the first and the second width and being spaced proximal about 6 to about 10 centimeters from the most proximal of the proximal ring electrode portion.

* * * * *